(12) United States Patent
Sane et al.

(10) Patent No.: US 10,287,597 B2
(45) Date of Patent: May 14, 2019

(54) WOUND INDUCIBLE EXPRESSION CONSTRUCT AND A METHOD OF ITS PREPARATION

(71) Applicant: Council of Scientific & Industrial Research, New Delhi (IN)

(72) Inventors: Aniruddha Prafullachandra Sane, Lucknow (IN); Saurabh Prakash Pandey, Lucknow (IN); Amar Pal Singh, Lucknow (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 15/538,954

(22) PCT Filed: Apr. 29, 2015

(86) PCT No.: PCT/IN2015/050033
§ 371 (c)(1),
(2) Date: Jun. 22, 2017

(87) PCT Pub. No.: WO2016/103279
PCT Pub. Date: Jun. 30, 2016

(65) Prior Publication Data
US 2018/0037901 A1    Feb. 8, 2018

(30) Foreign Application Priority Data
Dec. 23, 2014    (IN) .......................... 3865/DEL/2014

(51) Int. Cl.
*C12N 15/82*    (2006.01)
*C07K 14/415*    (2006.01)

(52) U.S. Cl.
CPC ........ *C12N 15/8237* (2013.01); *C07K 14/415* (2013.01); *C12N 15/8205* (2013.01); *C12N 15/8239* (2013.01); *C12N 15/8257* (2013.01); *C12N 15/8286* (2013.01); *Y02A 40/162* (2018.01)

(58) Field of Classification Search
None
See application file for complete search history.

(56) References Cited

U.S. PATENT DOCUMENTS 7,790,960 B2 * 9/2010 Jansens .............. C12N 15/8286
800/302
2003/0221216 A1    11/2003 Jansens et al.

FOREIGN PATENT DOCUMENTS

WO    2003093483    11/2003

OTHER PUBLICATIONS

"Annual Report 2011-2012" CSIR-National Botanical Research Institute, Lucknow, India, 2012, XP002743770, the whole document.
Database EMBL [Online], Jun. 24, 2006, "W_W6_C07_05 W Rosa wichurana cDNA clone W6C07, mRNA sequence.", XP002743769, retrieved from EBI accession No. EMBLEC589671, Database accession No. EC589671 sequence.
Corresponding International Search Report and Written Opinion for PCT/IN2015/050033 dated Aug. 31, 2015. WO.

* cited by examiner

*Primary Examiner* — Cynthia E Collins
(74) *Attorney, Agent, or Firm* — The Belles Group, P.C.

(57) ABSTRACT

The present invention provides a wound inducible expression construct and a method of its preparation. The invention provides a methods for isolation of an early wound inducible promoter that is activated within 5 minutes of any form of wounding (mechanical or biological) and a process of making transgenic plants in which expression of GUS/Insecticidal protein is regulated by Promoter (I.D.1) in a wound inducible manner for local expression of a chimeric gene used in this method and plants obtained thereby, and to the process for obtaining resistance to insect feeding.

5 Claims, 5 Drawing Sheets
Specification includes a Sequence Listing.

Wound induction in transgenic Arabidopsis

PED control 1    Line-10-3    Line-3-3    Line-9-3

Fig 5

1 prick = 1 mm²

| Cry1Ac Transgenic | Surface area of leaf disc | Expression of Cry/177 mm² | Expression of Cry/1 mm² |
|---|---|---|---|
| 35 S cryFl | 177 mm² | 24.8 ng | 0.14 ng |
| RbPCD1 pro (5 min wounded) | 177 mm² | 111.24 ng | 0.628 ng |
| RbPCD1 pro (20 min wounded) | 177 mm² | 571.71 ng | 3.23 ng |

SEQUENCE LISTING

```
<160> NUMBER OF SEQ ID NOS: 3

<210> SEQ ID NO 1
<211> LENGTH: 523
<212> TYPE: DNA
<213> ORGANISM: Artificial sequence
<220> FEATURE:
<223> OTHER INFORMATION: Rosa bourboniana

<400> SEQUENCE: 1
taaccgctag gcagtgagcc ggtaggtgaa aaacttaggc atgttaaaga ctagtcttgt      60
tttcattttt gtttttaat gaagtttcca aggtagacaa aagctctaaa gcccaggaca     120
gcataggata ctatctcttt taagtctttt cctaagcaaa tagtaagata cgaaaatgtt     180
ggtgcatttg ggcataatac atagaatttt tgggcatacg ggaaataccc cttttgaac     240 actgtattct cgtcattccg cttatcgttt tacttttacc atctgaaaaa gaagggagtt     300
gtcaaaaaaa ttgagccatt tttaccgccc tgcttggcta agttcacatg ctgttgtttc     360
cttgatctta tccgattgct ttcctccaat aacaacgcca cacgtacccc acaaacccac     420
agagaataaa acaaaatgcg tcccaccttg accttaaata gagcaacaat tcttacacac     480
tgatcccata agcagttcca agtttcaggt aacagagaag aag                       523

<210> SEQ ID NO 2
<211> LENGTH: 19
<212> TYPE: DNA
<213> ORGANISM: Artificial sequence
<220> FEATURE:
<223> OTHER INFORMATION: Primer

<400> SEQUENCE: 2
taaccgctag gcagtgagc                                                   19
```

```
<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
cttcttctct gttacctgaa a                                              21
```

WOUND INDUCIBLE EXPRESSION CONSTRUCT AND A METHOD OF ITS PREPARATION

CROSS-REFERENCE TO RELATED APPLICATIONS

This application is a U.S. national stage application under 35 U.S.C. § 371 of PCT Application No. PCT/IN2015/050033, filed Apr. 29, 2015, which claims priority to Indian Patent Application No. 3865/DEL/2014, filed Dec. 23, 2014, the entireties of which are incorporated herein by reference.

FIELD OF THE INVENTION

The present invention relates to a wound inducible expression construct and a method of producing plants in which expression of any available natural or commercial gene, which can be translated in to a functional protein, such as but not restricted to GUS or an insecticidal protein in very short time. This expression is regulated by an early novel wound inducible RbPCD1 (*Rosa bourboniana*) promoter of SEQ ID NO:1. Invention further relates to identification and isolation of this novel promoter RbPCD1 by using a set of forward primer GSP1 and reverse primer GSP2 of SEQ ID NO:2 and SEQ ID NO:3 respectively as given below.

```
GSP1
5'-TAACCGCTAGGCAGTGAGC-3'

GSP2
5'-CTTCTTCTCTGTTACCTGAAA-3'
```

PRIOR ART OR BACKGROUND ART

Plant productivity is affected by several factors, one of the major ones being insect damage. Both chewing and sucking pests feed on plant leaves, shoots, roots, fruits, flowers and grains leading to considerable loss of yield. Insect infestation is one of the major concerns for crop production. In this regard, it is necessary to develop novel approaches to reduce crop losses to insects and thereby increase net yield. Genetic transformation is a powerful tool for production of crop plants with increased resistance to phytopathogens. A number of transgenic cultivars with elevated tolerance to economically important pests and disease agents are in commercial production. However, in most of these the transgene is driven by a powerful constitutive promoter, such as the cauliflower mosaic virus 35S (CaMV 35S) promoter and its derivatives, and is expressed at high levels even in the absence of pathogen invasion. Continuous synthesis and high accumulation of transgene products, especially toxins, could interfere with plant metabolic pathways and the overall expression of other valuable traits and reduce yields. The above mentioned strategies, although effective, are associated with several problems that affect yield such as:

- Abnormalities in plant growth (leading to yield penalty) due to high level expression of the toxic proteins which even affect normal plant development (Barton et al., 1987; Diehn et al., 1996; Rocher et al., 1998; Sachs et al., 1998; Rawat et al., 2011).
- Reduced frequency of transgene incorporation in many plants (due to high levels of toxic protein that affect regeneration) as a result of which a much larger number of calli have to be created to get the requisite number of transformants (Rawat et al., 2011).
- Reduced expression of insecticidal protein at times of flowering (especially with the most commonly used CaMV35S promoter, which shows reduced expression at the time of flowering) in plants like cotton and maize leading to susceptibility to insect attack during flowering and boll formation by boll worm which reduces yields (Kranthi et al., 2005).
- Diversion of vital plant resources towards maintaining high levels of toxic protein even when they are not needed.

In contrast, the use of promoters of plant defensive genes has distinct advantages because most of them are activated only when the plant is attacked by pests or pathogens. The use of native plant promoters can also help to avoid transgene silencing often associated with the presence of promoters of non-plant origin in the plant genome and particularly the CaMV35S promoter [Matzke et al., Plant Physiol. 107 (1995) 679-685]. Plants have developed a variety of physical and biochemical defense barriers against pests and pathogens. Mechanical wounding of plant tissue (mimicking pathogen invasion or insect chewing) leads to the accumulation of mRNAs that encode proteins thought to be involved in plant defense [Bowles, Annu. Rev. Biochem. 59 (1990) 873-907], and provides a convenient system to isolate and study defense-related genes and their upstream regulatory regions in transgenic host. Some of the promoters developed include the AoPR1 promoter from *Asparagus* that is activated in 6 hours (Warner et al., 1993; Gulbitti-Onarici et al., 2009), the Shpx6B promoter from *Stylosanthes humili* speroxidise gene which is activated in 24-48 hours after insect feeding (Perrera and Jones, 2004). However, the time taken for activation of these promoters (6-48 hours) is rather long considering that insects take a much shorter time to feed on and initiate damage on plants. Thus identification of strong wound inducible promoters that express target proteins rapidly only at the time of wounding and their utilization for expression of insecticidal proteins is desirable.

Limitation in Prior Art

Presently no wound inducible promoter has been identified that is activated within a very short time (5-20 minutes) of wounding for rapid synthesis of any protein or chemical and that can act against both types of insects (chewing as well as sucking). Hence there was need to isolate wound specific promoter in plants, which gets activated quickly and preferably in 5-20 minutes.

Objectives

The main objective of the present invention is to provide a wound inducible expression construct and a method to develop transgenic plants which show quick response to wounds caused by biological/mechanical reasons. Here quick response means expression of gene under control of novel promoter RbPCD1 within 5-20 minutes.

Another objective of the invention is to develop insect resistant transgenic plants having a strong mechanical/biological wound inducible promoter which is isolated by synthetically designed primers that allows high level expression of the target protein within 5-20 minutes of wounding (by insects and other biotic pests).

Another objective of the invention is to develop method for developing insect resistant plants by using plant expression vector having RbPCD1 promoter of SEQ ID NO:1.

Yet another objective of the invention is to develop a method of identification and isolation of wound inducible promoter.

Yet another objective of the invention is to develop a method to study the tissue specificity of the promoter in presence and absence of wounding and during normal plant growth.

Yet another objective of the invention is to develop a method to validate the wound induction of the promoter in diverse plant families of economic importance representing both monocot and dicot kingdoms for universality of expression and use.

Yet another objective of invention to have transgenic plants having a promoter of SEQ ID NO:1 with different insecticidal toxic genes that are effective against both chewing and sucking pests.

Yet another objective of the invention is to express any gene and obtain high levels of any protein or enzyme within 5-20 minutes using the promoter with SEQ ID NO:1.

Yet another objective is to test the efficacy of the promoter by expression of an insecticidal toxin protein under its control in a wound inducible manner.

Yet another objective to have transgenic plants with controlled expression of insecticidal gene only under wounding to ensure normal plant development and to allow several other plants which are currently not so easily transformed due to insect protein toxicity to be transformed.

Yet another objective is to develop a process for reduced load on the plant by synthesizing the toxic protein only at the time of insect infestation/wounding and not at all times when it is not needed.

Yet another objective is to develop a process for construct preparation under control wound inducible promoter.

Yet another objective to develop a method of *Agrobacterium* mediated plant transformation of the above said construct.

SUMMARY OF THE INVENTION

Accordingly, the present invention provides an early wound inducible promoter which is activated in a very short time interval (5-20 minutes) by any form of wounding (mechanical or biological) using novel synthetically designed sets of primers of SEQ ID NO:2 and SEQ ID NO:3 from Rose for making transgenic plants having desirable gene under control of this promoter. This gene may be insecticidal protein encoding genes but not restricted to it.

Further the present invention relates to a method for identification and isolation of a strong wound inducible promoter of SEQ ID NO:1 which is activated within a very short time interval (5-20 minutes) after mechanical/biological wounding. A particular embodiment of present invention, relates to a method for obtaining early wound induced expression of desired proteins such as GUS/Cry proteins in monocotyledonous as well as dicotyledonous plants. The invention also relates to development of insect resistant plants against chewing or sucking type of insects. The present invention provides expression of an insecticidal protein or any desired protein in a wound inducible manner. In one embodiment a DNA sequence that represents the proximal promoter and 5' untranslated region of the programmed cell death like gene (RbPCD1) from the fragrant variety of rose (*Rosa bourboniana*) is isolated using the primer set of SEQ ID NO:2 and I.D.3. The DNA sequence of 523 nucleotides of SEQ ID NO:1 can drive the expression of any target gene situated downstream of the promoter at a high level in a wound inducible manner. The promoter is activated and leads to high level accumulation of the target protein within 5-20 minutes in response to any form of mechanical wounding (such as by a pin or forceps) or by excision of the leaf or stem tissue with a blade or by wounding caused by insect chewing or sucking or by tissue abrasion. Non significant or no expression is observed in absence of any form of wounding.

Transgenic plants like but not restricted to *Arabidopsis*, Tomato, Chickpea have been developed using a plant expressing vector having RbPCD1 promoter of SEQ ID NO:1 and demonstrated to act in these plants. It has also been demonstrated to act in plants like Rose, Cotton, Tobacco, and *Gladiolus* when it was introduced through agro-infiltration into these plants.

DETAILED DESCRIPTION

In the description of present invention, terms used has been defined below

Gene and Promoter: The term "gene" as used herein refers to segments of DNA located on genome and it contains the codes for the production of specific proteins. A gene consists of a long combination of four different nucleotide bases (chemicals) that are: A, T, C, and G. Any 3 nucleotides out of four make a code for amino acid called codon (with the exception of TAG, TGA and TAA). There are many possible combinations of four nucleotides. Typically in any plant cell, the 5'UTR (5' untranslated region), the coding region and the 3' UTR (3' untranslated region) are transcribed into RNA by a process called transcription (regulated by a sequence of regulatory region of DNA called promoter), of which, in case of a protein coding gene, the coding region is translated into protein. A gene may also have an additional sequence called intron (non coding region) that is removed prior to translation to a protein. In addition, every gene has a different promoter consisting of a long set of nucleotides upstream of the 5' UTR that is not translated but is required to control the expression of the gene of interest. In the present case the promoter region is required in a gene (cry1Ac) used for transformation in the current invention.

Chimeric Gene: The term "chimeric gene" refers to any artificial gene constructed by juxtaposition of fragments of unrelated genes or other DNA segments, which may themselves have been altered and that are not naturally associated with each other and/or originate, for example in current invention RbPCD1 and cry1Ac both are from different sources.

Genome: A term "genome" of a plant refers to the order of genes and DNA sequences (promoters) in a haploid set of chromosomes.

Foreign nucleic acid: The term "presence of a suitable foreign nucleic acid molecule" as used herein refers to any foreign nucleic acid molecule that is present in cells of said transgenic plant but absent from the cells of the corresponding source plant (*Arabidopsis*/Tomato). Thereby encompassed are nucleic acid molecules, e.g. gene sequences, which differ from a corresponding nucleic acid molecule in the source plant cell. Furthermore encompassed by the term "foreign" are nucleic acid molecules which are homologous with respect to the source plant cell but are situated in a different chromosomal location or differ, e.g., by way of a reversed orientation for instance with respect to the promoter. In principle, the nucleic acid molecule to be introduced in accordance with the present embodiment may be of any conceivable origin. It may be from any organism which comprises such molecules. Furthermore, it may be synthetic or derived from naturally occurring molecules by, e.g., modification of its sequence, i.e. it may be a variant or derivative of a naturally occurring molecule. It is, e.g., possible to change the sequence of a naturally occurring molecule so as to match the preferred codon usage of plants, in particular of those plants in which the nucleic acid molecule shall be expressed.

Induced expression: The term "induced expression" refers to a situation where gene expression is obtained or increased by a physical treatment, treatment with a chemical compound or exposure to environmental stimuli. In the current invention the exposure relates to mechanical wounding/biological wounding.

Insecticidal: "Insecticidal" is used herein to mean a substance toxic to insects that attack crops. In the current invention the Cry1Ac protein encoded by the cry1Ac gene is used as the insecticidal protein.

Complementary Sequence: Nucleic acid base sequences that can form a double-stranded structure by matching base pairs; the complementary sequence to G-T-A-C is C-A-T-G.

RbPCD1: This represents abbreviation of a *Rosa bourboniana* programme cell death like gene and promoter.

Expression vector: An expression vector, otherwise known as an expression construct, is usually a plasmid, phagemid or virus designed for protein expression in cells (Plant or Bacterial).

Expression cassette: An expression cassette is a part of a vector DNA used for cloning and transformation. In each successful transformation, the expression cassette directs the cells' machinery to make RNA and protein. An expression cassette is composed of one or more genes and the sequences controlling their expression. Three components comprise an expression cassette: a promoter sequence (in current invention, RbPCD1 promoter), an open reading frame (in current invention, cry1Ac or GUS gene), and a 3' untranslated region that, in eukaryotes, usually contains a polyadenylation site.

Biotic and abiotic wounding: Biotic wounding is a stress that occurs as a result of damage done to plants by other living organisms, such as herbivores including insects, nematodes, arthropods, fungi, bacteria, viruses etc on the other hand abiotic wounding is stress that occurs as a result of damage done to plants by other non living means including cold, heat, puncture or scratch made by scalpel, blade forceps etc.

Most of the scientific terms are defined, rest all technical and scientific terms used herein have the same meaning as commonly understood by one of ordinary skill in the art to which the compositions and methods described herein belong.

In an embodiment of the present invention it provides a wound inducible expression construct consisting of the nucleotide sequence of SEQ ID NO:1 or the complementary sequence of it along with the gene of interest useful for early activation of wound inducible promoter.

In an embodiment of the present invention it provides a construct where in the gene of interest is selected from the group comprising of insecticidal protein encoding genes against sucking and chewing pests like cry1Ac (and various crystal protein genes), anti-fungal genes like chitinases, genes encoding enzymes that synthesize low levels of medicinal compounds in plants.

In an embodiment of the present invention it provides a method for preparing the construct comprising of steps:
  i. providing RbPCD1 gene having SEQ ID NO:1;
  ii. amplifying SEQ ID NO: 1 using primers selected from, but not restricted to, GSP 1, and GSP 2 having SEQ ID NO:2, and SEQ ID NO:3;
  iii. ligating the gene of interest downstream to the promoter;
  iv. cloning the sequence obtained in step (iii) in suitable vector for plant expression In an embodiment of the present invention it provides a wound inducible promoter wherein the promoter gets activated within a very short time (5-20 minutes) of wounding.

In an embodiment of the present invention it provides a process for making transgenic plants comprising wound inducible promoter containing construct wherein the process comprises transforming the expression construct into the plant using *Agrobacterium* mediated transformation;

In an embodiment of the present invention it provides the process wherein the gene of interest is selected from the group comprising of those encoding insecticidal proteins, enzymes, antibodies, therapeutic proteins or any protein responsible for producing a valuable chemical comprising wounding of transgenic plants.

The present invention provides transgenic plants with the ability to express any desired gene within a very short time of mechanical or biological wounding. This expression is due to the wound inducible DNA sequence of 523 nucleotides of SEQ ID NO:1, representing the partial upstream portion of the programmed cell death like gene (RbPCD1) promoter and including the 5' untranslated region (UTR) isolated from rose using the novel designed synthetic sets of primers of SEQ ID NO:2 and I.D.3. The isolated DNA sequence of 523 nucleotides acting as promoter, can drive the expression of any target gene situated downstream of the promoter at a high level in a wound inducible manner. This promoter of SEQ ID NO:1 is activated and leads to high level accumulation of the target protein within very short time (5-20 minutes) in response to any form of mechanical wounding (such as by a pin or forceps) or by excision of the leaf/stem tissue with a blade or by wounding caused by insect chewing or sucking or by tissue abrasion. Very little or no expression is observed in absence of wounding. In one embodiment, the amplified fragment was sequenced and cloned into pBI101 (a promoter less binary vector) upstream of the beta glucuronidase gene at the SalI site. In another embodiment the chimeric fragment (crylAc gene under control of wound inducible RbPCD1 promoter) was cloned in to another pBI101 at the HindIII and EcoRI restriction sites in order to create a plant transformation construct. In another embodiment of the present invention, the wound inducible construct was introduced into Agrobacterium tumefaciens by freeze thaw and electroporation methods respectively. Agrobacterium cells containing the wound inducible construct was grown in a culture flask and Arabidopsis, tomato and chickpea plants were transformed by floral dip, Agrobacterium mediated genetic transformation using leaf disc and cotyledonary methods respectively using this construct. Several independent transgenic plants were raised and screened for the transgene by polymerase chain reaction as well as by their ability to grow on kanamycin (used as a selection antibiotic to remove untransformed plants). Transgenic plants were grown to $T_1$, $T_2$ and $T_3$ generations by self crossing in case of Arabidopsis while tomato plants were grown to $T_0$, $T_1$ and $T_2$ generation by self crossing and seeds collected in each generation.

Development of stable transgenic plants through tissue culture is still a major problem in grain legumes so in an embodiment of present invention we have raised several independent transgenic shoots of chickpea ($T_0$ generation) using explants.

Arabidopsis and tomato plants were grown on soilrite and normal autoclaved soil respectively. All plants were watered on alternate days with water or Hoagland solution. Chickpea shoots were grown on MS (Murashige and Skoog) medium containing respective hormones. Leaves of transgenic Arabidopsis and chickpea plants from the progeny of homozygous lines and $T_0$ lines respectively were wounded by rapid pin pricks and kept for 5 minutes and 20 minutes and GUS expression was monitored by histochemical staining using glucuronic acid (1 mg/ml) in a solution containing phosphate buffer (pH 7.2) for its activity. The leaves were kept for 3 hours for colour development in the presence of cycloheximide (1.8 mM or 0.5 mg/ml) in an X-Gluc containing phosphate buffer solution after 5 minutes and 20 minutes of wounding for colour development. Cycloheximide (an inhibitor of protein synthesis) was used to ensure that the colour observed represented only the protein that was produced during the period of wounding. This ensured that whatever blue colour was observed was due only to protein synthesized during the 5 mM and 20 minute time course and not later during the development of colour. Wound inducible expression was seen from early stage of development when seedlings were a few days old right up to when plants started senescing. Expression was seen in stem, leaves, other parts of plant (except roots) only upon wounding while in flowers abscission zone expression was found without wounding.

In another embodiment of the current invention the promoter was next tested for universality of expression in different plants of economic importance. Besides transgenic Arabidopsis (family Brassicaceae, a representative of Brassica/cabbage family), transgenic chickpea (family Leguminaceae, a representative of the legume family) and transgenic tomato (a representative of the Solanaceae family), other plants such as cotton (Malvaceae), tobacco (Solanceae), Rose (a representative of Rosaceae family) and Gladiolus (a representative of the monocot kingdom) were also transiently transformed by Agrobacterium inoculation through a syringe (containing the Agrobacterium transformed with the wound inducible promoter containing construct). For agroinjection, plant tissues were kept for two days on the plant for integration of the Agrobacterium and the tissues then wounded by pin punctures. Histochemical GUS assay for checking GUS expression was performed as described above. As shown in drawings strong wound inducible expression could be seen in transgenic Chickpea, Arabidopsis and Tomato leaves as well as in agroinjected Cotton sepals, Rose petals, Gladiolus tepals and Tobacco leaves only at the site of wounding. Transgenic plants were raised with the use of CaMV35S constitutive promoter expression vector taken as control to compare the efficacy of wound inducible promoter.

Further in another embodiment of this invention, to ensure the functionality of the promoter, transgenic Arabidopsis and Tomato plants were raised using wound inducible construct having crylAc gene under the control of RbPCD1 promoter by the same method (Agrobacterium mediated) as described above. The expression of the crylAc gene (full length or C-terminal truncated) under the RbPCD1 promoter of SEQ ID NO:1 in transgenic Arabidopsis and Tomato plants led to normal plant development and seed set. Plants expressing RbPCDpro:cryIAcFL killed H. armigera larvae feeding on these plants within 8 hours of release on the plant compared to 24 hours in plants expressing the crylAc gene under the CaMV35S promoter.

Thus, the transgenic plants were protected against insects by the wound inducible expression of controlling amount of insecticidal protein Cry1Ac. By controlling it is meant that a toxic (lethal) or combative (sub-lethal) amount of toxic protein is produced. At the same time, the plants are morphologically normal and may be cultivated in the usual manner for human consumption should the Cry1Ac protein be deemed as safe for human health. In another embodiment of the invention, expression of insecticidal protein in plants (Arabidopsis/Tomato), was tested before and after wounding using an ELISA assay and found that the basal level of expression of Cry1Ac is low (0.0049 ng/mm$^2$) compared to 0.14 ng/mm$^2$ under the CaMV35S promoter. However within 5 minutes of wounding the expression rises to 5 fold (6.28 ng/mm$^2$) higher than in CaMV35S lines in lowest expressing transgenic lines. According to this aspect of invention, plants such as Arabidopsis/Tomato are provided that are insect resistant due to presence in their genome of foreign DNA comprising a DNA sequence encoding an insecticidal protein, under control of a wound inducible promoter of SEQ ID NO:1 which ensures expression in wounded tissue. According to one embodiment of the invention, expression of an insecticidal protein in the plants is such that, in the absence of wounding, the insecticidal protein is expressed at low or undetectable levels while upon feeding by insects, it is increased rapidly (within 5 minutes) in the wounded tissue to a level which is sufficient to kill the feeding insect. The present invention further relates to use of the wound inducible promoter not only against chewing insects but also against sucking pest provided a gene that encodes a product toxic to sucking pests is used downstream of the promoter.

Different methods such as sandwich ELISA (using Cry1Ac coated antibody) can be used to determine the wound induced expression of Cry1Ac protein in transgenic plants of *Arabidopsis*/Tomato that were raised. In particular, according to the present invention the expression of Cry1Ac protein was checked in every puncture made by a forceps in a leaf disc of unit area with a diameter of 1.5 cm upon wounding. For the present embodiment of current invention, different number of punctures (2 pricks, 4 pricks, 8 pricks and 12 pricks) of wounds (intended to mean mechanical damage) were made in the intact leaves of individual transgenic lines and kept for different time intervals (5 minutes and 20 minutes) following which the leaf discs were immediately frozen for protein isolation. Unwounded transgenic leaf discs were taken as control. Expression level of insecticidal protein is expressed as the percentage of soluble protein as determined by antibody specific sandwich ELISA as described herein related to the total amount of soluble protein (as determined by Lowry method). An ELISA is useful in the current invention for the correct estimation of wound induced Cry1Ac protein by one prick.

An aspect of present invention provides for a wound inducible expression construct comprising RbPCD1 promoter of SEQ ID NO:1 or a complementary sequence thereof along with a gene of interest.

Another aspect of the present invention provides for a wound inducible construct as herein described, wherein the gene of interest is selected from the group comprising of insecticidal protein encoding genes against sucking and chewing pests like crylAc (and various crystal protein genes), anti-fungal genes like chitinases, genes encoding enzymes that synthesize low levels of medicinal compounds in plants.

Another aspect of the present invention provides for a wound inducible construct as herein described wherein the promoter is activated within a very short time (5-20 minutes) of wounding.

Another aspect of the present invention provides for a a method of preparing wound inducible expression construct, said method comprising the steps of:

(a) isolating the RbPCD1 promoter gene;

(b) amplifying RbPCD1 promoter gene of step (a) using primers selected from, but not restricted to, GSP 1, and GSP 2 having SEQ ID NO:2, and SEQ ID NO:3;

(c) obtaining a 523 nucleotide fragment of SEQ ID NO:1;

(d) ligating the SEQ ID NO:1 of step (c) upstream of gene of interest in a expression cassette; and (e) inserting the expression cassette of step (d) in a plant expression vector.

Another aspect of the present invention provides for a method of preparing wound inducible construct as herein described wherein the gene of interest is selected from group comprising of insecticidal protein encoding genes against sucking and chewing pests like crylAc (and various crystal protein genes), anti-fungal genes like chitinases, genes encoding enzymes that synthesize low levels of medicinal compounds in plants Another aspect of the present invention provides for a method of preparing wound inducible construct as herein described wherein the gene of interest is expressed in both monocotyledonous and dicotyledonous plants.

Another aspect of the present invention provides for a transgenic plant comprising of a wound inducible expression construct, wherein the wound inducible expression consist of RbPCD1 promoter having SEQ ID NO:1 or a complementary sequence thereof along with a gene of interest.

Another aspect of the present invention provides for a the transgenic plant as herein described, wherein the gene of interest is selected from the group comprising of insecticidal protein encoding genes against sucking and chewing pests like crylAc (and various crystal protein genes), anti-fungal genes like chitinases, genes encoding enzymes that synthesize low levels of medicinal compounds in plants.

Another aspect of the present invention provides for a the transgenic plant as herein described, wherein the target proteins are expressed only at the time of wounding.

Another aspect of the present invention provides for a the transgenic plant as herein described, wherein the promoter present in the wound inducible construct is activated within a very short time (5-20 minutes) of wounding.

Another aspect of the present invention provides for a method for making transgenic plant said method comprising the steps of:

(a) preparing a wound inducible construct comprising RbPCD1 promoter of SEQ ID NO:1 or a complementary sequence thereof along with a gene of interest;

(b) inserting the construct of step (a) in a *Agrobacterium;*

(c) transforming the *Agrobacterium* of step (b) in the plants; and (d) obtaining a transgenic plant comprising and expressing a construct of step (a).

Another aspect of the present invention provides for a method for making transgenic plant as herein described, wherein the gene of interest is selected from the group comprising of insecticidal protein encoding genes against sucking and chewing pests like crylAc (and various crystal protein genes), anti-fungal genes like chitinases, genes encoding enzymes that synthesize low levels of medicinal compounds in plants.

Another aspect of the present invention provides for a method for making transgenic plant as herein described, whenever in the transgenic plant the wound inducible construct is activated within a very short duration of wounding i.e. within 5-20 mins. of wounding.

Another aspect of the present invention provides for a method for making transgenic plant as herein described, wherein the transgenic plant has the ability to express any gene interest within a very short time of wounding.

Another aspect of the present invention provides for use of a wound inducible expression construct comprising RbPCD1 promoter of SEQ ID NO:1 or a complementary sequence thereof along with a gene of interest useful for early activation of wound inducible promoter.

Another aspect of the present invention provides for use of a wound inducible expression construct comprising RbPCD1 promoter of SEQ ID NO:1 or a complementary sequence thereof along with a gene of interest for preparing transgenic plants.

Another aspect of the present invention provides for use of a wound inducible expression construct as herein described, wherein the transgenic plants expressing gene of interest within short time of wounding (within 5-20 mins of wounding).

Another aspect of the present invention provides for use of transgenic plant for expression construct comprising RbPCD1 promoter of SEQ ID NO:1 or a complementary sequence thereof along with a gene of interest.

Another aspect of the present invention provides for use of transgenic plant as herein described, wherein the transgenic plant expresses gene of interest within short time of wounding (within 5-20 mins of wounding).

Another aspect of the present invention provides for the use of novel wound inducible constructing for preparation and/developing transgenic plants, wherein the said method involves (a) preparing a wound inducible construct comprising comprising RbPCD1 promoter of SEQ ID NO:1 or a complementary sequence thereof along with a gene of interest; (b) inserting the construct of step (a) in a *Agrobacterium*; (c) transforming the *Agrobacterium* of step (b) in the plants; and (d) obtaining a transgenic plant comprising and expressing a construct of step (a).

Another aspect of the present invention provides for use of novel wound inducible, wherein the wound inducible construct enable immediate and fast expression of gene of interest. The wound inducible promoter is activated within 5-29 mins of physical or chemical wound injury and it is because of which the gene of interest also present in the construct gets activated. Thus the present invention in its one of the embodiment also provides the use of wound inducible promoter for preparing transgenic plants capable of fast or immediate expression of gene of interest in the transgenic plants when they receive a chemical or mechanical or biological wound.

EXAMPLES

The present invention will now be more fully described with reference to the accompanying examples and drawings. It should be understood, however, that the following description is illustrative only and should not be taken in any way as a restriction on the generality of the invention described above.

The following non limiting examples describe the construction of suitable chimeric foreign gene including a DNA sequence encoding an insecticidal protein under the control of early wound inducible promoter for the expression of insecticidal protein under it and obtaining a resistance against *Helicoverpa armigera*. Unless stated otherwise in examples, all techniques are carried out according to standard protocols as described in Sambrook and Russell Molecular cloning: A Laboratory Manual, Second Edition, Cold Spring Harbor Laboratory Press, NY, in volumesl, 2 and 3 of Ausubel et al., (1989).

Example 1

Preparation of Genome Walking Library & Isolation of RbPCD1 Promoter of SEQ ID NO:1:
Preparation of Genome Walking Library:
The genome walking library of rose was constructed from rose petal DNA digested with DraI, EcoRV, PvuII, StuI and SmaI using standard protocols of BD Genome Walker Universal Kit (BD Biosciences Clontech, USA). In brief, 2.5 μg genomic DNA each was subjected to digestion with five different restriction enzymes such as DraI, EcoRV, PvuII and StuI and SmaI, in separate 1.7 ml microfuge tubes. Tubes were kept at 37° C. overnight and a small proportion was checked on 0.6% agarose gel to ensure proper digestion of DNA. Subsequently, reaction mixtures were extracted with phenol:chloroform and precipitated by adding 1/10 volume of 3M sodium acetate (pH 4.5), 2 volume of ice cold 95% ethanol. DNA from each tube was pelleted by centrifugation at 15,000×g for 10 min, the pellet was washed with 100 μl of ice cold 80% ethanol, vacuum dried and suspended in 20 μl of TE (Tris 10 mM, EDTA 1 mM, pH 8.0). From each tube, 4 μl was taken in separate tube and 1.9 μl of Genome walker adapter (25 μM), 0.8 μl of 10× ligation buffer and 0.5 μl of T4 DNA Ligase (6 U/μl) and 0.8 μl of H$_2$O were added in each tube separately and incubated at 16° C. overnight. The ligation reaction was stopped by placing all the tubes at 70° C. for 5 min.

Isolation of RbPCD1 Promoter of −523nt of SEQ ID NO:1:
Primary PCR:
Primary PCR was performed using Genome-walker library of rose with AP1 as adapter primer (designed in vitro) and GW-GSP1 primers of RbPCD1. In primary PCR, components were added as follows: sterile water 30 μl, genome-walker library 4 μl (containing a mixture of all 5 libraries), 10×PCR buffer 5 μl, 10 mM dNTP 5 μl, 12.5 picomoles each of AP1 and GSP1 primers (2.5 μl each) and (1 U/μl) Klen Taq DNA Polymerase 1 μl. The PCR was initiated by 7 cycles of denaturation step at 94° C. for 2 sec and extension at 72° C. for 3 min, followed by 32 cycles of amplification each consisting of denaturation at 94° C. for 2 sec, annealing at 67° C. for 3 min followed by a final extension at 67° C. for 4 min.

Secondary PCR:
For secondary amplification, 5 μl of the amplified reaction of primary PCR was diluted to 500 μl with sterile MQ H$_2$O, and 2 μl of this was used as template for secondary PCR amplification. The reaction conditions were as above, except that instead of GSP1 and AN, the primers used were GSP2 (a gene specific reverse primer internal to GSP1) and AP2 (a truncated adapter primer). The PCR was initiated by 5 cycles of denaturation step at 94° C. for 2 sec and extension at 72° C. for 3 min, followed by 20 cycles of amplification each consisting of denaturation at 94° C. for 2 sec, annealing at 67° C. for 3 min followed by a final extension at 67° C. for 4 min Amplified fragments were resolved on agarose, excised, purified and cloned in pTZ57R/T using the InsT/A cloning kit from Thermo scientific and sequenced.

Example 2

Figure 1:
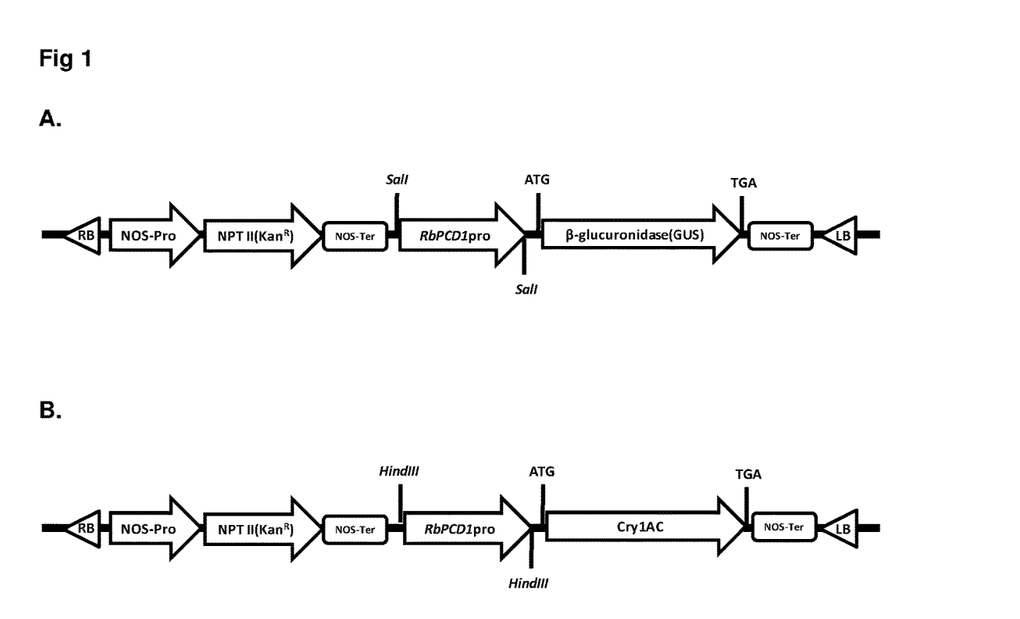
FIG. 1 A schematic presentation of the RbPCD1 promoter construct for plant transformation. Restriction sites relevant for cloning are in italics (SalI and HindIII). (A) Construct (pBI101-RbPCD1pro::GUS) for GUS gene expression under RbPCD1 promoter of SEQ ID NO:1 cloned at SalI restriction enzyme site (B) Construct (pBI101-RbPCD1pro::Cry1Ac) for cry1Ac gene expression under RbPCD1 promoter of SEQ ID NO:1 cloned at HindIII restriction enzyme site.

Preparation of Wound Inducible Construct:
Amplified −523 nt fragment of RbPCD1 promoter of SEQ ID NO:1 was primarily cloned into pTZ57R/T [InsTAclone PCR cloning kit, Cat. No. #1241, Thermo scientific, Lithuania (EU)] and sequenced, then sub cloned into the pBI101 vector (a promoter less binary vector—Clontech laboratories, USA; Cat No 6017-1) upstream of the beta glucuronidase gene (GUS-gene present within pBI101, from Clontech laboratories, USA, Cat No 6017-1) at the SalI site. In another construct, the amplified 523 nt fragment of RbPCD1 promoter was cloned in HindIII digested pTZ57R/T and then sub cloned at HindIII restriction site upstream to full length crylAc gene (obtained with permission from Dr PK Singh/RK Tuli's lab, CSIR-NBRI) in the plant expression vector pBI101 (FIG. 1). The resultant pBI101 carrying the wound inducible chimeric expression cassette was transformed into *Arabidopsis*, tomato and chickpea via *Agrobacterium tumefaciens* strain GV3101 (strain GV3101pMP-90RK from DNA Cloning Services, Germany, Cat No 1004).

Example 3

Process of Making Transgenic *Arabidopsis*, Tomato and Chickpea:
Transformation of *Arabidopsis* Plants by Floral Dip Method
*Arabidopsis* (*Arabidopsis* Biological Resource Centre, Ohio State University, USA) plants were grown and when the secondary bolts started to flower, plants were transformed with recombinant plasmid constructs by floral dip method as described by Clough and Bent (1998). For this a single colony from plate containing *Agrobacterium tumefa-*

*ciens* GV3101 strain carrying gene of interest was picked and inoculated in 5 ml LB medium supplemented with antibiotics rifampicin (50 µg/ml), kanamycin (50 µg/ml) and gentamycin (30 µg/ml). The primary culture was grown at 28° C., 220 rpm for 24 h. From this 1 ml culture was inoculated in 500 ml of LB medium containing the same set of drugs and grown for 24 hours at 28° C., 220 rpm. Cells were harvested by centrifugation at 5000×g for 5 min at room temperature. Pellet was resuspended gently in 5% sucrose solution to a final $OD_{600}$ of approximately 1. Prior to dipping, the detergent Silwet L-77 (Lehle Seeds, USA) was added in *Agrobacterium* cell suspension prepared in 5% sucrose, to a final concentration of 0.05% and mixed gently by swirling the container. This solution was termed as infiltration medium. The floral inflorescences were dipped in the infiltration medium for 10 to 15 sec with gentle swirling. A film of liquid coating the plant was seen and excess liquid was wiped off. Dipped plants were placed in dark under a dome or cover for 16 to 24 h to maintain high humidity and then back in the racks and subjected to normal light. For a higher rate of transformation, the same plants with newer flowers were again dipped in a fresh suspension of recombinant *Agrobacterium*. Plants were allowed to grow and moisture of soil was maintained with nutrient medium till all the siliques had grown fully. As the siliques began to dry, watering of plants was stopped and seeds were allowed to become mature. The dried seeds were harvested, separated from other dried tissues and stored at room temperature in dry place. The dried seeds/transformants were selected using antibiotic Kanamycin (50 mg/ml) on half MS agar plate as selection marker. Transformants were identified as Kanamycin resistant seedlings that produced green leaves and well established roots in the selection medium. Viable seedlings were transferred into the individual pots filled with soilrite saturated with nutrient media. Pots were kept in plastic trays and the plants were left to grow in normal conditions. Transformed plants were further confirmed by PCR with gene specific primers using genomic DNA as template.

*Agrobacterium* Mediated Genetic Transformation of Tomato Plants:

Tomato seeds (National Seed Corporation Ltd., Pusa Campus, New Delhi) were surface sterilized with 50% sodium hypochlorite (bleach) containing 0.1% Tween-20 in a laminar flow hood for 5 mins. After that seeds were washed thoroughly with sterile Milli-Q water for 4-5 times. The surface sterilized seeds were blotted on Whatmann filter paper and allowed to germinate in seed germination medium (half strength MS medium) under culture room conditions at 25° C. Tomato transformation was carried out using 1 month old plants having large number of expanded leaves. Young expanded leaves were excised and several small discs cut out with sterile blade in order to increase infection opportunity of *Agrobacterium* and to enhance transformation efficiency. The leaves were placed in MS medium, precultured for 24 to 48 h at 25° C. under low light conditions (10 µEm-2s-1). On the same day a single colony of *Agrobacterium* containing the construct was inoculated in 5 ml LB/YEB medium with appropriate antibiotics for 16-18 h at 28° C. 50 µl of this culture was used to inoculate bacteria in 25 ml YEB with antibiotics (Rifampicin+Gentamycin and Kanamycin) and allowed to grow to an O.D. 0.2-0.4 at 600 nm. The bacterial culture was centrifuged at 5000 rpm for 5 min at 4° C. The pellet was resuspended in liquid half strength MS basal medium and acetosyringone was added at a concentration of 200 µM to enhance the infection efficiency. Pre-incubated leaf explants were co-cultivated with *Agrobacterium* culture (8-10 ml) for 25 min with occasional swirling. The explants were then dried on sterile Whatmann paper and incubated in co-cultivation medium in culture room in dark for 2 days. Explants were then transferred onto plates containing MS medium supplemented with 0.1 mg/l IAA+1.0 mg/l BAP+1.0 mg/l Zeatinriboside or 0.1 mg/l IAA+1.0 mg/l Zeatinriboside+50 mg/l Kanamycin and 500 mg/ml cefotaxime for 6 to 7 days to eliminate *Agrobacterium* contamination and support explant growth. The explants were kept for callusing and shoot initiation on the same medium in culture room conditions for 2-3 weeks. At the time of third selection calli were transferred for shooting by increasing auxin concentration and lowering down cytokinin concentration (0.5 mg/l IAA+0.25 mg/l Zeatinriboside) for selection of elongated transformants Elongated shoots were then transferred to rooting medium having 25 mg/l kanamycin and cefotaxime for 12-15 days. Rooted plants were both hardened in KNOPS solution for 1 week as per standard protocol or directly transferred to soil and finally shifted to glass house for optimum growth.

*Agrobacterium* Mediated Genetic Transformation of Chickpea Plants:

The mature healthy seeds of chickpea (*C. arietinum* L.-CSIR-NBRI field) were surface sterilized (0.01% $HgCl_2$ and dipped 30 sec in 70% ethanolfollowed by washing with 3-4 times $H_2O$) and incubated for germination in culture medium, consisting of Murashige and Skoog (MS) salts, B5 vitamins, 3% (w/v) sucrose, 0.8% (w/v) agar and 1.0 mg/l 6-benzylaminopurine (BAP). The cultures were incubated in the culture room maintained at 24±1° C. under cool white light of intensity 60 mmol $m^2s^{-1}$ for 16 h photoperiod. A single positive colony from plate containing *Agrobacterium tumefaciens* GV3101 strain carrying a chimeric wound inducible cassette of interest was picked and inoculated in 5 ml YEB medium supplemented with antibiotics rifampicin (50 µg/ml), kanamycin (50 µg/ml) and streptomycin (30 µg/ml). The primary culture was grown at 28° C., 220 rpm for 24 h. From this 50 µl culture was inoculated in 25 ml of YEB medium containing the same set of drugs and grown for 24 hours at 28° C., 220 rpm and harvested, the bacterial pellet was resuspended in liquid MS medium to obtain an $OD_{600}$ nm between 0.8 to 1.0. Various cotyledonary nodes were excised with sterile scalpel, sonicated for 30-60 sec, vacuum infiltrated for 5 min and infected in Agrobacterial suspension for 20 min with constant shaking at 75 rpm 24° C. The cotyledonary nodes were blotted on sterile filter paper and incubated on semi-solid MS medium supplemented with appropriate plant growth regulators and incubated in dark for 2 days under culture room conditions. After co-cultivation for a period of 2-4 days, the cotyledonary nodes were transferred to Petri dishes having MS medium supplemented with required plant growth regulators (PGRs) and 250-500 mg $l^{-1}$ cefotaxime and cultured one week under normal growth conditions. The cotyledonary nodes were sub-cultured for two week on medium supplemented with 50 or 100 mg $l^{-1}$ kanamycin along with the appropriate amounts of PGRs and 100-250 mg $l^{-1}$ cefotaxime. The emerging shoots from the cotyledonary nodes cultured on kanamycin-supplemented medium for 3 successive cycles for screening of transformants. Shoots obtained were clonally propagated on shoot elongation medium, prior to rooting or grafting. The rooted or grafted plant stocks were processed for hardening and acclimatization, before their transfer to glasshouse for further growth, development and molecular characterization. To test the transgene integration, DNA was isolated from the small piece of tissue taken from shoots and PCR reaction performed by using respective primers.

Example 4

Histochemical Analysis of Transgenic Lines for Transgene Integration

Figure 2:
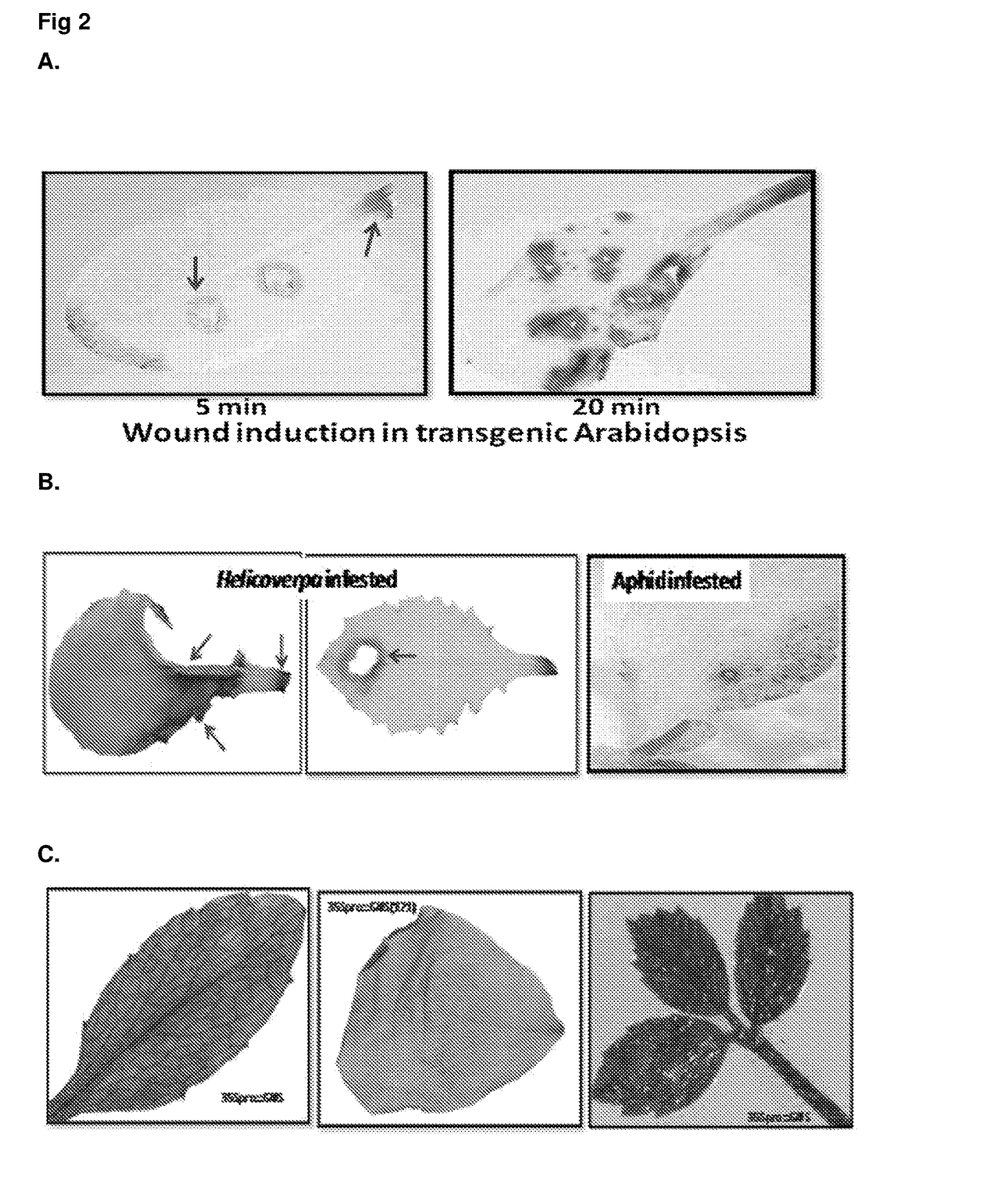
FIG. 2. Illustrates the histochemical analysis of GUS expression of RbPCD1 promoter of SEQ ID NO:1 and pBI121 vector as control. (A) represents 5 min, 20 min *Arabidopsis* wounded leaf (Colour development was carried out for 3 h in presence of cycloheximide), (B) represents GUS activity in *Helicoverpa armigera* and Aphid fed transgenic *Arabidopsis* lines (C) GUS activity in pBI121 vector transformed *Arabidopsis*, chickpea transgenic lines and agroinfiltrated rose petal (D) Agro-infiltration and histochemical GUS analysis of RbPCD1promoter-GUS in rose petals, cotton sepal, *gladiolus* tepal and tobacco leaves and in stable transgenic shoots of chickpea after wounding. (E) GUS activity during plant development in *Arabidopsis* transgenic lines.

Histochemical GUS staining was carried out as described by Gattolin et al., (2006). Tissue samples of different plants (All plants—obtained from CSIR-NBRI garden except *Arabidopsis* and tomato) were incubated in 1 mg/ml X-gluc (Biosynth AG, Switerland) solution containing 50 mM sodium phosphate buffer pH 7.2, 0.5 mM $K_3Fe(CN)_6$ and 0.5 mM $K_4Fe(CN)_6$ for 16-24 h at 37° C. After incubation tissues were destained in 70% ethanol at 37° C. and stored until examination. Light microscopy was performed on a Leica Wild M3Z microscope (Leica Germany). As shown in drawings, the histochemical GUS assay of the RbPCD1 promoter showed strong wound induction in response to mechanical wounding as well as insect wounding (*Helicoverpa armigera* and aphid-obtained from chickpea fields of CSIR-NBRI and raised in entomology lab) in transgenic *Arabidopsis* leaves (FIG. 2 *a* & *b*). Apart from *Arabidopsis*, a strong wound inducible expression could be seen in transgenic chickpea as well as in agroinjected cotton sepals, rose petals, *Gladiolus* tepals and tobacco leaves only at the site of wounding (FIG. 2*d*). However, a uniform GUS expression throughout the whole plant including leaf could be seen in transgenic plants expressing GUS gene under the CaMV35S promoter in plants transformed with expression vector pBI121 (pBI121, GUS driven by CaMV35S promoter-Clontech laboratories, USA 0018-1) and used as control to compare the efficacy of wound inducible promoter (FIG. 2*c*).

In order to examine the spatiotemporal expression patterns of RbPCD1pro::GUS, whole plants at different developmental stages were histochemically stained. A strong wound inducible expression was seen from early stage of development when seedlings were a few days old right up to flowering stage while wound inducible expression decreased when plants started senescing. Expression was seen in stem, leaves, other parts of plant (except roots) only upon wounding while in flower abscission zones expression was found without wounding (FIG. 2*e*).

Example 5

ELISA Assay of Transgenic Lines and Insect Mortality Assay (DAS-ELISA)
(Double Antibody Sandwich Enzyme Linked Immunosorbent Assay)

Quantitative estimation of protein produced in transgenic *Arabidopsis* and tomato plants was performed using a Double Antibody Sandwich Enzyme Linked Immunosorbent Assay (DAS-ELISA-Agdia Inc USA, Cat No PSM 14900/0480) with pre-antibody coated wells in microtitre plates. To check the expression of Cry1Ac protein under the wound inducible promoter which expresses within 5-20 minutes, intact leaves of transgenic plants were wounded with a pair of forceps (1 mm$^2$) by rapid pricking and after that leaf discs were made by using chopper of diameter size approximately 1.5 cm. Control (unwounded) leaf discs were immediately frozen and wounded leaf disc tissues taken 5-20 minutes after wounding followed by protein isolation using protein extraction buffer. For protein isolation, leaf discs were crushed in liquid nitrogen and PBST [NaCl-8.0 g, sodium diphosphate, dibasic (anhydrous)-1.15 g, potassium phosphate monobasic (anhydrous)-0.2 g, potassium chloride-0.2 g, Tween-20-0.5 g, pH 7.4 (dissolved in 900 ml double distilled water)] and kept at 4° C. for 10 min. Extraction buffer along with the protein extract was centrifuged at 12000×g for 10 min at 4° C. Supernatent was taken and added to the kit wells of 100 µl and kit antibody of 100 µl added and incubated at 37° C. for 2 h. This was then washed with PBST buffer for 5-6 times. To this, 100 µl of peroxidase substrate solution was added and incubated at 37° C. for 10-15 min and read at 650 nm. To calculate the amount of Cry1Ac protein expressed per wound the respective ODs were plotted against Standard Cry Plot.

Example 6

Transient Expression of Promoter by Agroinjection to Test its Efficacy in Other Plants The promoter fragments, cloned in pBI101 upstream to GUS were used to determine the expression. These promoters were transiently expressed in different plants by agro-infiltration. Agro-injection was performed as described by Orzaez et al. (2006) with few modifications. In brief, a single colony of *Agrobacterium* strain GV3101 harbouring the promoter construct was inoculated in 5 ml LB medium containing selective antibiotics rifampicin (50 mg/ml), kanamycin (50 mg/ml) and gentamycin (30 mg/ml) and grown overnight at 28° C. at 200 rpm. From this culture, 1 ml was transferred to 50 ml induction medium (LB medium supplemented with 0.5% Sucrose, 2 mM $MgSO_4$, 20 mM acetosyringone, 10 mM MES, pH 5.6 plus same set of antibiotics) and grown overnight at same condition to an $OD_{600}$ of 1.4. Cells were recovered by centrifugation at 5000×g for 5 min at RT, resuspended in infiltration medium (10 mM $MgCl_2$, 10 mM MES, 200 mM acetosyringone, pH 5.6; optical density 1.0) and incubated at room temperature with gentle agitation (50 rpm) for a period of 2 h. For agro-injection, control rose flowers (with only two or three petals from the outer whorl open), *gladiolus* tepals, cotton sepals and tobacco leaves were selected and a needle (size 23, dimensions 0.63325 mm) fitted on to a 2 ml syringe (filled with the 0.5 ml recombinant agrobacterial suspension containing 0.01% acetosyringone) was lightly inserted in the bottom of the petals, sepal and through mid rib of the tobacco leaves. The agrobacterial suspension was slowly forced into the Rose petals, *gladiolus* tepals, tobacco leaves, cotton sepals and allowed to infiltrate all through the respective tissue up to the point of attachment of the petal/tepal with the thalamus and of the leaf with the stem. Agroinjection was performed with three flowers per construct and three petals per flower and three leaves per plant. The excess suspension was wiped off and the buds were kept for 2 days on the plant. As a control, Agrobacteria containing pBI101 (no promoter), pBI121 (GUS driven by CaMV35S promoter), were also used for agro-infiltration of independent tissues. After two days from agro-infiltration, flowers/sepals/tepals/leaves were punctured with pair of forceps and carefully cut out under water. After wounding, the petals, tepal, sepals and leaves were detached and stained for GUS expression as described above.

Example 7

Figure 3:
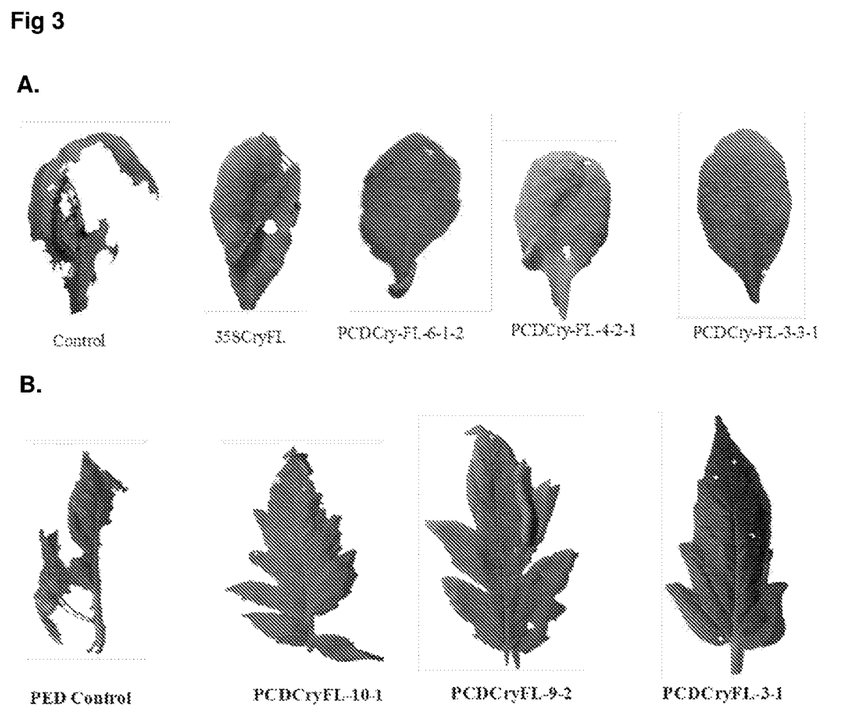
FIGS. 3.(A) & (B) Detached leaf insect bioassay of *Arabidopsis* and tomato transgenic lines expressing Cry1Ac protein under RbPCD1 promoter of SEQ ID NO:1 fed upon by the insect *Helicoverpa armigera* at different stages of growth.
Figure 4:
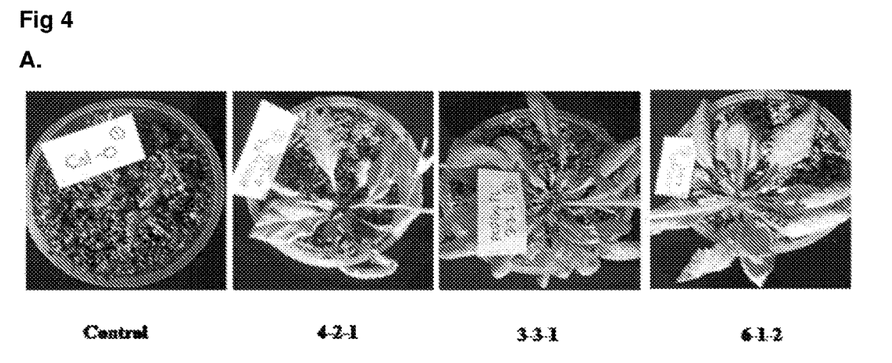
FIGS. 4.(A) & (B) Insect bioassay of *Arabidopsis* and tomato transgenic lines expressing Cry1Ac protein under RbPCD1 promoter with $3^{rd}$ instar larva of the insect *Helicoverpa armigera* on intact plant leaf.
Figure 5:
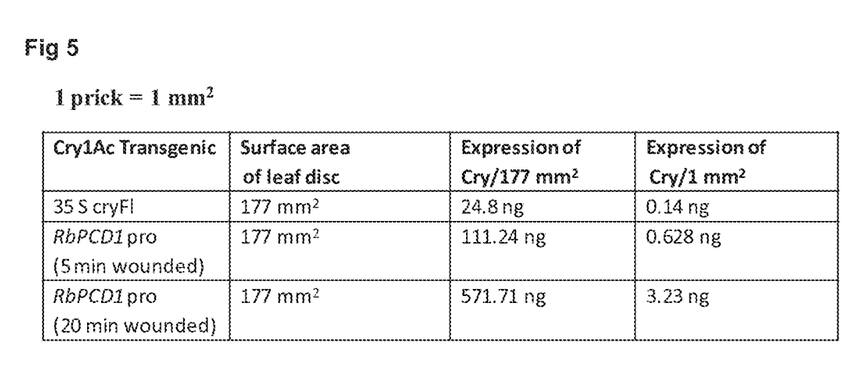
FIG. 5 Table represents comparative expression of Cry1Ac protein under RbPCD1 promoter and CaMV35S constitutive promoter measured by ELISA.

To check the effectiveness of putative transgenic (*Arabidopsis* and Tomato) plants expressing crylAc under the control of wound inducible RbPCD1 promoter against insect attack, detached leaf as well as whole plant insect bioassays were conducted with different larval stages of insect *Helicoverpa armigera*. Toxicity of transgenic plants due to expression of Cry1Ac protein for insect was analyzed by conducting no choice insect bioassays on detached leaf as well as whole plant on T₁ and homozygous (T₃) lines of *Arabidopsis* while primary transformants (T₀) and T₁ generation plants were selected for tomato. Comparison of cry1Ac expression and mortality in transgenic plants were performed against cry1Ac expressed under constitutive CaMV 35S promoter in transgenic *Arabidopsis* plants and wild type Col-0 used as control. For tomato plants, non-transformed wild type plants were used as control. As shown in drawings, the result of the insect bioassay showed that the wound inducible expression of cry1Ac in transgenic *Arabidopsis* and tomato conferred complete protection against *Helicoverpa armigera* in comparison to non-transgenic control plants (FIGS. 3 & 4).

Advantages/Uses

The promoter has several advantages over the other known promoters such as CaMV35S that is used for constitutive expression of insecticidal toxin proteins.

1. It will increase the efficacy of several insecticidal toxin protein genes that are currently in use for controlling Lepidopteran insects by ensuring low level expression of the toxic genes during normal plant growth but much higher level expression (as compared to the CaMV35S promoter) at the time of insect wounding. The low level expression under non wounded conditions during normal plant growth (in absence of insect attack) would prevent the deleterious effects of the high levels of toxic protein on whole plant development (seen under the CaMV35S promoter) and ensure normal plant development and higher yields.
2. The promoter would ensure high level expression of the protein even after wounding at the flowering and late fruiting stages (beyond 90 days (as evident from expression in cotton sepals) which is currently not possible in maize and cotton due to inherent low level expression of the CaMV35S promoter at the reproductive stages.
3. The promoter would be effective against both chewing and sucking pests since it is activated by wounding by both these types of insects. It thus has a wide canvas for controlling damage by biotic stress.
    Examples: Cotton, chickpea and other legumes, *Brassica* family members (like *Arabidopsis*), Solanaceae family members like tomato, tobacco etc, monocots like *Gladiolus*.
4. The control of the insecticidal gene expression only under wounding would ensure normal plant development and may allow several other plants, which are currently not so easily transformed due to insect protein toxicity, to be transformed.
5. It will reduce the load on the plant by synthesizing the toxic protein only at the time of insect infestation/wounding and not at all times when it is not needed.
6. It would be useful for rapid and high level expression of valuable proteins in a wound inducible manner
7. It would be useful for rapid expression of any medicinal or valuable chemical that requires prior action by a protein or enzyme.

We claim:

1. A wound inducible expression construct comprising a promoter having the sequence of Sequence ID No. 1 or the complementary sequence of it and a heterologous gene of interest.

2. The construct as claimed in claim 1, wherein the gene of interest is selected from the group consisting of genes encoding insecticidal proteins against sucking and chewing pests, antifungal genes and genes encoding enzymes that synthesize medicinal compounds in plants.

3. A method for preparing the construct as claimed in claim 1 comprising the steps of:
   i. amplifying the promoter using template DNA comprising SEQ ID NO:1 and primers GSP 1, and GSP 2 having the sequence of SEQ ID No.2, and SEQ ID No.3 respectively:
   ii. ligating the gene of interest downstream to the promoter; and
   iii. cloning the ligated gene of interest and the promoter obtained in step i. in a suitable vector.

4. A process for making a transgenic plant, the process comprising transforming a plant with the expression construct as claimed in claim 1, using *Agrobacterium* mediated transformation to obtain the transgenic plant.

5. The process as claimed in claim 4, wherein the gene of interest is selected from the group consisting of genes encoding insecticidal proteins against sucking and chewing pests, anti-fungal genes and genes encoding enzymes that synthesize medicinal compounds in plants.

* * * * *